US00PP09552P

United States Patent [19]

Trees

[11] Patent Number: Plant 9,552

[45] Date of Patent: May 14, 1996

[54] GERANIUM PLANT NAMED 'LILAC CHIFFON'

[75] Inventor: Scott C. Trees, Arroyo Grande, Calif.

[73] Assignee: Geo. J. Ball, Inc., West Chicago, Ill.

[21] Appl. No.: 431,424

[22] Filed: May 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

The new and distinct *Pelargonium×hortorum* cultivar named 'Lilac Chiffon' is provided. This new Zonal Geranium was the result of a controlled breeding program wherein the a plant designated 3412-21 (non-patented in the United States) was pollinated by the 'Precious' cultivar (U.S. Plant Pat. No. 8,005). The new cultivar forms attractive soft lilac semi-double florets with a white eye. Medium green foliage with zonation is well retained during shipment. A vigorous self-branching growth habit is exhibited that does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'Lilac Chiffon'.

The new cultivar is a product of a planned breeding program which had the objective of the creation of a Geranium cultivar that exhibits uniform flowers, medium green foliage, a medium self-branching growth habit that requires no growth regulator, a propensity for rapid rooting, and stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated 3412-21 (non-patented in the United States) which exhibits single lavender florets with dark green foliage. The male parent (i.e., pollen parent) was the 'Precious' cultivar (U.S. Plant Pat. No. 8,005) which exhibits semi-double light lavender florets with white eyes and medium green foliage. The parentage of the new 'Lilac Chiffon' cultivar can be summarized as follows:

3412-21×'Precious'.

'Lilac Chiffon' was discovered and selected during 1992 as a highly distinctive flowering plant from among the progeny of the stated cross at Arroyo Grande, Calif., U.S.A. This plant was initially designated BFP-1098.

It was found that the new cultivar of the present invention:

(a) exhibits attractive soft lilac semi-double florets with a white eye, (b) forms attractive medium green foliage with zonation, and (c) exhibits a vigorous self-branching growth habit in the absence of a growth regulator.

When plant material of the 'Lilac Chiffon' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of 'Lilac Chiffon' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of unique characteristics as herein described for the 'Lilac Chiffon' cultivar is fixed and is retained through successive generations of such asexual reproduction.

The new 'Lilac Chiffon' cultivar has not been observed under all possible environment conditions. Accordingly, the described phenotype may vary somewhat with variations in the environment, such as temperature, light intensity, and day length.

Of the many commercial cultivars, the 'Precious' cultivar (U.S. Plant Pat. No. 8,005) is considered to be the most similar to the new cultivar of the present invention. When the new cultivar of the present invention is compared to the 'Precious' cultivar, it is found that the 'Lilac Chiffon' cultivar exhibits a less compact growth habit (e.g., approximately 31 to 36 cm. in height vs. approximately 25 to 30 cm.), generally smaller florets (e.g., approximately 4.4 to 4.6 cm. vs. approximately 4.5 to 5.0 cm.), and generally more florets per umbel (e.g., approximately 24 to 39 vs. approximately 20 to 29). The 'Lilac Chiffon' cultivar additionally exhibits fewer petals, more petaloids, generally longer peduncles, and generally shorter internodes as specified in greater detail hereafter.

The new cultivar of the present invention is being marketed by Geo. J. Ball, Inc. under the Designer trademark.

BRIEF DESCRIPTION OF THE PHOTOGRAPHS

The accompanying photographs show the new 'Lilac Chiffon' cultivar with colors being as nearly true as it is reasonably possible to make the same in color illustrations of this character. The plants were being grown in greenhouses at West Chicago, Ill., U.S.A.

DETAILED DESCRIPTION

Figure 1:
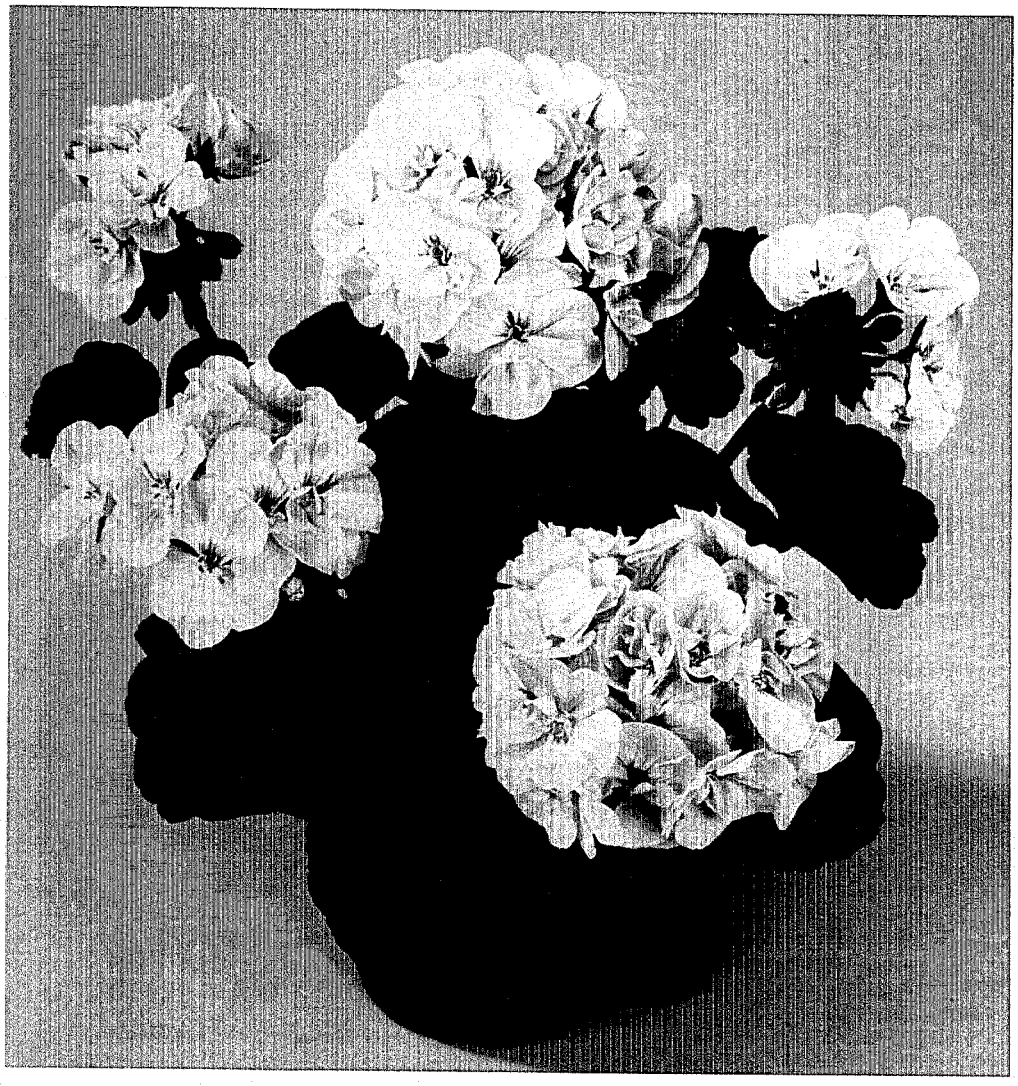
FIG. 1 illustrates the general appearance of an overall plant as seen primarily from above.
Figure 2:
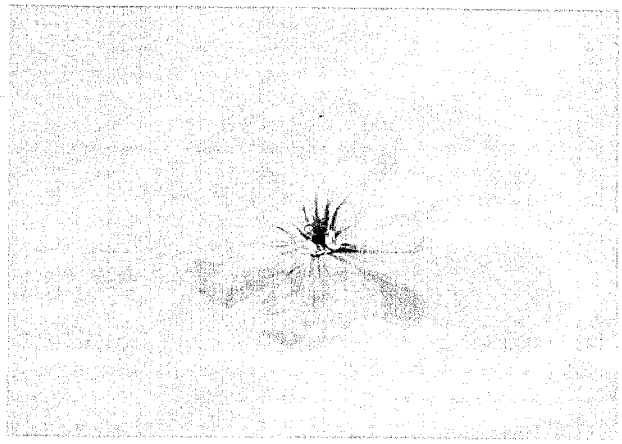
FIG. 2 illustrates the general appearance of a typical floret wherein the lavender coloration and white eye are shown.

The following observations, measurements and comparisons describe plants grown in Ball FloraPlant's greenhouses located at West Chicago, Ill., U.S.A., under conditions which approximate those generally used in commercial practice. In the following description, color references are made to the R.H.S. Colour Chart of The Royal Horticultural Society, London, England. The color values were determined between 11:00 and 11:45 a.m. on Jan. 3, 1995, under natural light conditions of 2,000 footcandles.

Classification:

*Botanical.*—*Pelargonium×hortorum* Bailey, cv. 'Lilac Chiffon'.

*Commercial.*—Zonal Geranium.

Inflorescence

A. Umbel:

*Average diameter.*—Approximately 9.0 to 10.0 cm. compared to approximately 8.0 to 10.0 cm for the 'Precious' cultivar (U.S. Plant Pat. No. 8,005).

*Average depth.*—Approximately 6.0 to 8.0 cm. compared to approximately 5.5 to 6.0 cm. for the 'Precious' cultivar.

*Peduncle length.*—Approximately 18.5 to 24.0 cm. compared to approximately 15.5 to 22.0 cm. for the 'Precious' cultivar.

*Pedicel length.*—Approximately 3.0 to 3.4 cm. compared to approximately 2.0 to 3.0 cm. for the 'Precious' cultivar.

*Number of umbels plant.*—When grown in a 10 cm. pot at 9 weeks after the sticking of a rooted cutting, there commonly are approximately 3 to 5 umbels per plant. The 'Precious' cultivar also commonly forms approximately 3 to 7 umbels per plant.

*Number of florets/umbel.*—When grown in 10 cm. pots at 9 weeks, approximately 24 to 39 florets per umbel commonly are formed. This compares to approximately 20 to 29 florets per umbel for the 'Precious' cultivar under the same growing conditions.

B. Corolla:

*Average diameter.*—Approximately 4.4 to 4.6 cm. compared to approximately 4.5 to 5.0 cm. for the 'Precious' cultivar.

*Form.*—Both the 'Lilac Chiffon' cultivar and the 'Precious' cultivar are semi-double with petaloids. The 'Lilac Chiffon' cultivar commonly possesses approximately 5 petals per floret, and the 'Precious' cultivar commonly possesses approximately 6 to 8 petals per floret.

*Number of petaloids.*—Commonly forms 4 to 5 petaloids per floret whereas the 'Precious' cultivar commonly possesses 1 to 3 petaloid per floret.

*Color.*—General tonality from a distance of three meters: Lavender with white eye. Adaxial: Purple Group 78C with an eye formed by a white area on each of the upper two petals. This compares to Purple Group 75A with a white area on each of the upper two petals for the 'Precious' cultivar. Abaxial: Purple Group 75C with attachment points of Red Purple Group 67B. This compares to Purple Group 75C for the 'Precious' cultivar.

C. Bud:

*Shape.*—Oval-pointed.

*Color.*—Adaxial: Purple Group 78D compared to Purple Group 75A for the 'Precious' cultivar. Abaxial: Purple Group 75C for both the 'Lilac Chiffon' cultivar and the 'Precious' cultivar.

D. Reproductive organs:

*Androecium.*—The anthers are commonly approximately 2.0 to 3.0 mm. in length. The pollen color is Orange-Red Group 31A for both the 'Lilac Chiffon' cultivar and the 'Precious' cultivar. The filaments are approximately 5.0 to 7.0 mm. in length compared to approximately 6.0 to 8.0 for the 'Precious' cultivar.

*Gynoecium.*—The pistil length commonly is approximately 9.0 mm. There is a single stigma which commonly has a length of approximately 3.5 mm. which commonly branches into 5 parts, and the style length is approximately 5.0 mm.

*Fertility.*—Commonly does not produce fruits in the absence of mechanical fertilization.

E. Spring flowering response period: Approximately 6 to 7 weeks from rooted cuttings under standard greenhouse conditions.

F. Outdoor flower production: Freely flowering under outdoor growing conditions with substantially continuous blooming.

G. Durability: Ships well.

Plant

A. Foliage: Medium green with zonation.

*Form.*—Reniform, with cordate base.

*Margin.*—Crenate.

*Color.*—Adaxial: Green Group 137C for at both the 'Lilac Chiffon' cultivar and the 'Precious' cultivar. Abaxial: Yellow-Green Group 146B for both the 'Lilac Chiffon' cultivar and the 'Precious' cultivar.

*Size.*—Approximately 9.2 to 10.6 cm. at the widest point and approximately 7.5 to 9.1 cm. at the narrowest point. This compares to approximately 8.5 to 10.4 cm. at the widest point and approximately 6.5 to 7.5 cm. at the narrowest point for the 'Precious' cultivar.

*Tolerance to Botrytis.*—In the field the 'Lilac Chiffon' exhibits more tolerance than the 'Precious' cultivar.

B. General appearance and form:

*Internode length.*—Commonly varies from approximately 1.8 to 2.3 cm. This compares to approximately 2.0 to 3.0 cm. for the 'Precious' cultivar.

*Branching pattern.*—Freely basal branching. No pinching is required to obtain self-branching. A vigorous self-branching growth habit is observed in the absence of a growth regulator.

*Height.*—Approximately 31 to 36 cm. above a 10 cm. pot at 9 weeks under standard greenhouse conditions. This compares to approximately 25 to 30 cm. for the 'Precious' cultivar.

I claim:

1. A new and distinct Geranium plant named 'Lilac Chiffons', substantially as herein shown and described, which:

(a) exhibits attractive soft lilac semi-double florets with a white eye, (b) forms attractive medium green foliage with zonation, and (c) exhibits a vigorous self-branching growth habit in the absence of a growth regulator.

* * * * *